US00PP21349P2

(12) United States Plant Patent
Bernuetz

(10) Patent No.: US PP21,349 P2
(45) Date of Patent: Sep. 28, 2010

(54) ***ARGYRANTHEMUM* PLANT NAMED 'BONMADLEM'**

(50) Latin Name: *Argyranthemum×hybrida*
Varietal Denomination: Bonmadlem

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 12/454,021

(22) Filed: May 11, 2009

(51) Int. Cl.
*A01H 5/00* (2006.01)

(52) U.S. Cl. ..... Plt./406

(58) Field of Classification Search ..... Plt./406, Plt./284

See application file for complete search history.

*Primary Examiner*—June Hwu
(74) *Attorney, Agent, or Firm*—C. A. Whealy

(57) ABSTRACT

A new and distinct cultivar of *Argyranthemum* plant named 'Bonmadlem', characterized by its upright, uniform and mounded plant habit; freely branching and vigorous growth habit; freely flowering habit; anemone-type inflorescences with light yellow-colored ray florets and bright yellow-colored disc florets; and good garden performance.

1 Drawing Sheet

Botanical designation: *Argyranthemum×hybrida.*
Cultivar denomination: 'BONMADLEM'.

BACKGROUND OF THE INVENTION

The present invention relates to a new and distinct cultivar of *Argyranthemum* plant, botanically known as *Argyranthemum×hybrida* and hereinafter referred to by the name 'Bonmadlem'.

The objective of the breeding program is to create new mounding and freely flowering *Argyranthemum* cultivars with attractive floret colors and good garden performance.

The new *Argyranthemum* plant originated from a cross-pollination made by the Inventor in May, 2004 in Yellow Rock, New South Wales, Australia of a proprietary selection of *Argyranthemum×hybrida* identified as code number 03-10, not patented, as the female, or seed, parent with a proprietary selection of *Argyranthemum×hybrida* identified as code number 03-15, as the male, or pollen, parent. The new *Argyranthemum* was discovered and selected by the Inventor as a single flowering plant within the progeny of the stated cross-pollination in a controlled environment in Yellow Rock, New South Wales, Australia in April, 2005.

Asexual reproduction of the new *Argyranthemum* plant by vegetative tip cuttings was first conducted in Yellow Rock, New South Wales, Australia in May, 2005. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible environmental conditions. The phenotype may vary somewhat with variations in environment such as temperature and light intensity, without, however, any variance in genotype.

The following traits have been repeatedly observed and are determined to be the unique characteristics of 'Bonmadlem'. These characteristics in combination distinguish 'Bonmadlem' as a new and distinct *Argyranthemum* cultivar:

1. Upright, uniform and mounded plant habit.
2. Freely branching and vigorous growth habit.
3. Freely flowering habit.
4. Anemone-type inflorescences with light yellow-colored ray florets and bright yellow-colored disc florets.
5. Good garden performance.

Plants of the new *Argyranthemum* differ from plants of the female parent selection in the following characteristics:

1. Plants of the new *Argyranthemum* are not as compact as plants of the female parent selection.
2. Plants of the new *Argyranthemum* have anemone-type inflorescences whereas plants of the female parent selection have single-type inflorescences.

Plants of the new *Argyranthemum* differ primarily from plants of the male parent selection in inflorescence form as pants of the new *Argyranthemum* have anemone-type inflorescences whereas plants of the male parent selection have double-type inflorescences.

Plants of the new *Argyranthemum* can be compared to plants of the *Argyranthemum×hybrida* 'Bonmadcrel', disclosed in U.S. Plant Pat. No. 18,650. In side-by-side comparisons conducted in Higashiomi, Shiga, Japan, plants of the new *Argyranthemum* differed from plants of 'Bonmadcrel' in the following characteristics:

1. Plants of the new *Argyranthemum* were larger than plants of 'Bonmadcrel'.
2. Inflorescences of plants of the new *Argyranthemum* had fewer ray and disc florets than inflorescences of plants of 'Bonmadcrel'.
3. Plants of the new *Argyranthemum* and 'Bonmadcrel' differed in ray and disc floret coloration.

BRIEF DESCRIPTION OF THE PHOTOGRAPHS

The accompanying photographs illustrate the overall appearance of the new *Argyranthemum* plant. These photographs show the colors as true as it is reasonably possible to obtain in colored reproductions of this type. Colors in the photographs may differ slightly from the color values cited in the detailed botanical description which accurately describe the colors of the new *Argyranthemum* plant.

The photograph at the top of the sheet comprises a side perspective view of a typical flowering plant of 'Bonmadlem' grown in a container.

The photograph at the bottom of the sheet is a close-up view of typical inflorescences of 'Bonmadlem'.

DETAILED BOTANICAL DESCRIPTION

The aforementioned photographs and following observations and measurements describe plants grown during the winter in Higashiomi, Shiga, Japan in a polyethylene-covered greenhouse and under conditions and practices which approximate those generally used in commercial potted *Argyranthemum* production. During the production of the plants, day temperatures ranged from 10° C. to 23° C. and night temperatures ranged from −2° C. to 6° C. Plants were pinched one time about eight weeks after planting. Plants used in the photographs and for the description were about four months old. In the following description, color references are made to The Royal Horticultural Society Colour Chart, 2001 Edition, except where general terms of ordinary dictionary significance are used.

Botanical classification: *Argyranthemum×hybrida* 'Bonmadlem'.

Parentage:

*Female, or seed, parent.*—Proprietary selection of *Argyranthemum×hybrida* identified as code number 03-01, not patented.

*Male, or pollen, parent.*—Proprietary selection of *Argyranthemum×hybrida* identified as code number 03-10, not patented.

Propagation:

*Type.*—By terminal cuttings.

*Time to initiate roots, summer.*—About seven days at temperatures of about 20° C. to 25° C.

*Time to initiate roots, winter.*—About ten days at temperatures of about 15° C. to 20° C.

*Time to produce a rooted young plant, summer.*—About three weeks at temperatures of about 20° C. to 25° C.

*Time to produce a rooted young plant, winter.*—About four weeks at temperatures of about 15° C. to 20° C.

*Root description.*—Fibrous; white in color.

*Rooting habit.*—Freely branching; moderately dense.

Plant description:

*Appearance.*—Herbaceous anemone-type potted *Argyranthemum*. Upright, uniform and mounded plant habit. Strong and freely branching growth habit with about eight primary lateral branches developing per plant; dense and full plants. Vigorous growth habit.

*Plant height.*—About 32.2 cm.

*Plant width.*—About 30 cm.

*Lateral branches.*—Length: About 19.4 cm. Diameter: About 2.7 mm Internode length: About 1.4 mm. Strength: Strong; young stems, flexible. Texture: Pubescent. Color: Close to 144A.

Foliage description:

*Arrangement.*—Alternate, simple.

*Length.*—About 7.3 cm.

*Width.*—About 3.5 cm.

*Shape.*—Obovate.

*Apex.*—Acute.

*Base.*—Cuneate.

*Margin.*—Pinnately-parted.

*Texture, upper and lower surfaces.*—Smooth, glabrous.

*Venation.*—Pinnate, reticulate.

*Color.*—Developing leaves, upper surface: Close to 137B. Developing leaves, lower surface: Close to 137C. Fully expanded leaves, upper surface: Close to 137A; venation, close to 138A. Fully expanded leaves, lower surface: Close to 137B; venation, close to 138A.

*Petiole.*—Length: About 2.3 cm. Diameter: About 2 mm Texture, upper and lower surface: Smooth, glabrous. Color, upper and lower surfaces: Close to 137A.

Inflorescence description:

*Appearance*—Anemone-type inflorescence form with narrowly elliptic-shaped ray florets and enlarged disc florets; solitary upright inflorescences borne on terminals above foliage; ray and disc florets arranged acropetally on a capitulum.

*Fragrance.*—Slightly fragrant, pleasant.

*Flowering season.*—Plants flower from spring through fall in Japan; flowering continuous during this period.

*Inflorescence longevity.*—Inflorescences last about 13 to 14 days on the plant; inflorescences persistent.

*Quantity of inflorescences.*—Freely flowering, about 50 inflorescences per plant branch at one time.

*Inflorescence bud.*—Height: About 7.4 mm. Diameter: About 7.1 mm. Shape: Ovoid. Color: Between 146A and N199A.

*Inflorescence size.*—Diameter: About 4.1 cm. Depth (height): About 1.5 cm. Diameter of disc: About 2.8 cm.

*Ray florets.*—Shape: Narrowly elliptic. Length: About 1.4 cm. Width: About 5.3 mm. Apex: Obtuse. Base: Obtuse. Margin: Entire. Texture, upper and lower surfaces: Smooth, glabrous. Number of ray florets per inflorescence: About 23 arranged in about two to three whorls. Color: When opening and fully opened, upper surface: Close to 1D. When opening and fully opened, lower surface: Close to 4D.

*Disc florets.*—Arrangement: Massed at center of receptacle. Shape: Tubular, enlarged. Apex: Obtuse. Length: About 1 cm. Diameter: About 2.2 mm. Number of disc florets per inflorescence: About 116 arranged in numerous whorls. Color, immature and mature: Close to 6A to 6B.

*Phyllaries.*—Number of phyllaries per inflorescence: About 25 arranged in several whorls. Length: About 5.7 mm. Width: About 2.6 mm. Shape: Ovate. Apex: Rounded to broadly acute. Base: Truncate. Margin: Entire. Texture, upper and lower surfaces: Smooth, glabrous; margins, papery. Color, upper and lower surfaces: Close to 144A.

*Peduncles.*—Length: About 6 cm to 9 cm. Diameter: About 1.3 cm. Angle: Mostly erect. Strength: Strong, flexible. Texture: Smooth, glabrous. Color: Close to 144A.

*Reproductive organs.*—Androecium: Present on disc florets only. Anther length: About 1 mm to 2.5 mm. Anther shape: Lanceolate. Anther color: Close to 16A. Pollen amount: None observed. Gynoecium: Present on both ray and disc florets. Pistil length: About 4.4 mm. Stigma shape: Two-parted. Stigma color: Close to 12B. Ovary color: Close to 144B.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 0° C. to about 30° C.

It is claimed:

1. A new and distinct *Argyranthemum* plant named 'Bonmadlem' as illustrated and described.

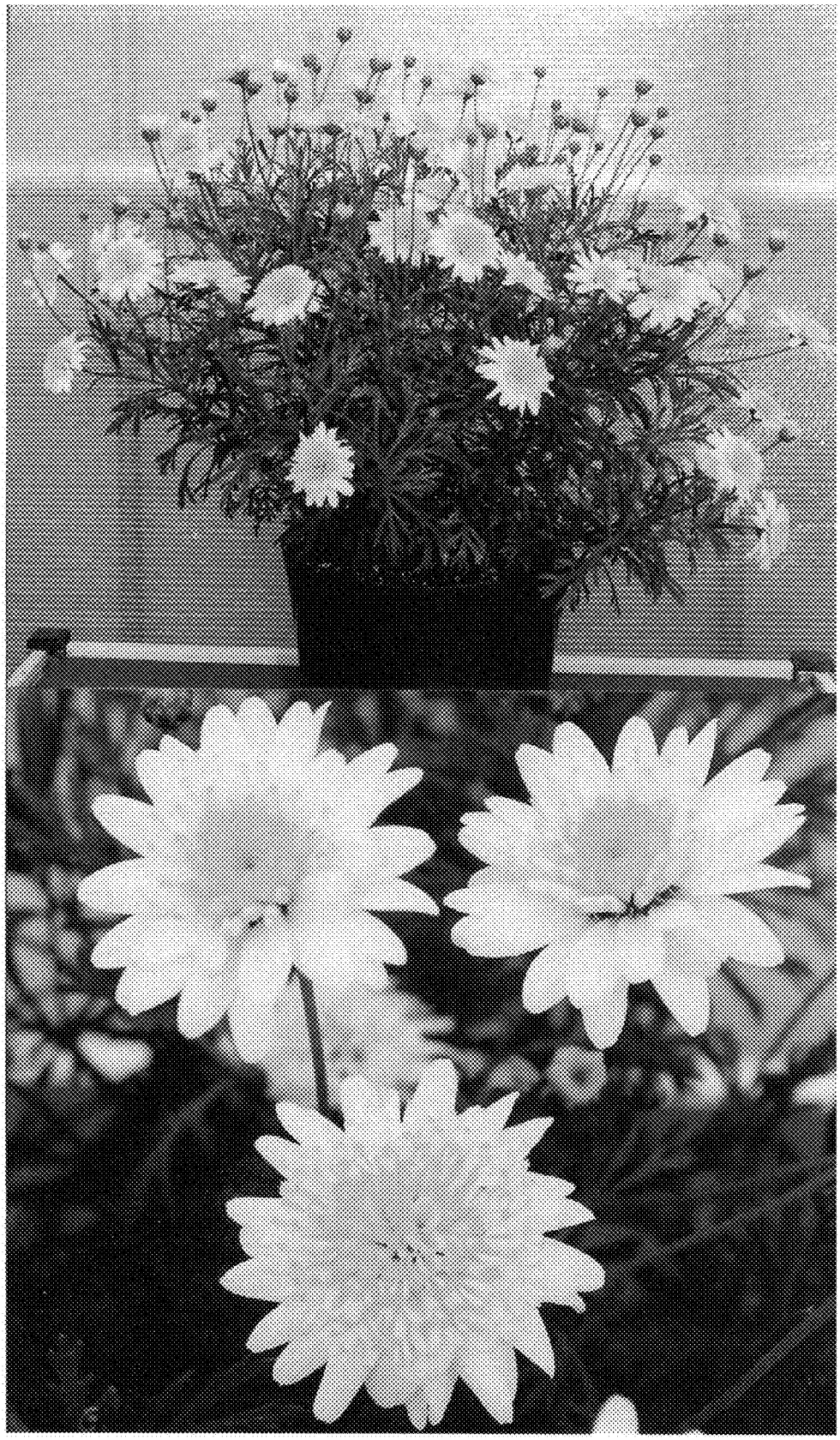

* * * * *